(12) United States Patent
Smith et al.

(10) Patent No.: US 7,179,590 B2
(45) Date of Patent: Feb. 20, 2007

(54) HIGH TEMPERATURE REVERSE TRANSCRIPTION USING MUTANT DNA POLYMERASES

(75) Inventors: Edward Soh Smith, San Francisco, CA (US); Carita Maria Elfstrom, San Francisco, CA (US); David Harrow Gelfand, Oakland, CA (US); Russell Gene Higuchi, Alameda, CA (US); Thomas William Myers, Alameda, CA (US); Nancy Jeneane Schönbrunner, Moraga, CA (US); Alice Ming Wang, Lafayette, CA (US)

(73) Assignee: Roche Molecular Systems, Inc, Alameda, CA (US)

( * ) Notice: Subject to any disclaimer, the term of this patent is extended or adjusted under 35 U.S.C. 154(b) by 0 days.

(21) Appl. No.: 09/823,649

(22) Filed: Mar. 30, 2001

(65) Prior Publication Data

US 2002/0012970 A1   Jan. 31, 2002

Related U.S. Application Data

(60) Provisional application No. 60/198,336, filed on Apr. 18, 2000.

(51) Int. Cl.
*C07H 21/04* (2006.01)
*C12Q 1/68* (2006.01)

(52) U.S. Cl. .................... 435/6; 435/91.1; 435/91.2; 435/91.21; 536/23.1

(58) Field of Classification Search ................ 435/6, 435/91.1; 530/300, 327; 536/23.1, 23.2
See application file for complete search history.

(56) References Cited

U.S. PATENT DOCUMENTS

| 5,310,652 | A | | 5/1994 | Gelfand et al. ............ 435/6 |
|---|---|---|---|---|
| 5,374,553 | A | * | 12/1994 | Gelfand et al. .......... 435/252.3 |
| 5,561,058 | A | | 10/1996 | Gelfand et al. |
| 5,614,365 | A | | 3/1997 | Tabor et al. |
| 5,830,714 | A | * | 11/1998 | Swaminathan et al. .... 435/91.2 |
| 5,968,799 | A | * | 10/1999 | Gelfand et al. ............ 435/194 |
| 6,015,668 | A | | 1/2000 | Hughes et al. |
| 6,083,686 | A | | 7/2000 | Sullivan |
| 6,346,379 | B1 | * | 2/2002 | Gelfand et al. ............ 435/6 |

FOREIGN PATENT DOCUMENTS

| EP | 0 482 714 | | 4/1992 |
|---|---|---|---|
| EP | 0 655 506 | | 5/1995 |
| EP | 0 823 479 A3 | | 2/1998 |
| EP | 0 902 035 A2 | | 3/1999 |
| EP | 0 902 035 A3 | | 6/1999 |
| WO | WO 92/06202 | * | 4/1992 |
| WO | WO 95/14770 | | 11/1994 |
| WO | WO 95/14770 | | 6/1995 |
| WO | WO 98/40496 | | 9/1998 |
| WO | WO 00/71739 | | 11/2000 |

OTHER PUBLICATIONS

Kawasaki. "Amplfiication of RNA" PCR Protocols, Chapter 3, pp. 21-28, 1990.*
Maniatis et al. "Molecular Cloning." 1983, pp. 213-215.*
Myers, T. W. et al, "Amplification of RNA: High Temperature Reverse Transcription and DNA Amplification With Thermus Thermophilus DNA Polymerase", *PCR Strategies*, 1995, Chapter 5: 58-68.
Selner, Loryn and Turbett, Gavin, "*Comparison of Three RT-PCR Methods,*" BioTechniques (1998) 25:230-234 (Royal Perth Hospital).
Tse, William T., et al., "*Reverse Transcription and Direct Amplification of Cellular RNA Transcripts by Taq* Polymerase, " Gene (1990) 88:293-296 (0378-1119/90).
Beckman, Robert A., et al., "*On the Fidelity of DNA Replication: Manganese Mutagenesis in Vitro,* " Biochemistry (1985) 24:5810-5817 (0006-2960/85).
Leung, David W., et al., "*A Method for Random Mutagenesis of a Defined DNA Segment Using a Modified Polymerase Chain Reaction,*" Technique (1989) vol. 1, 1:11-15 (1043-4658/89).
Brown, D.M., "*Basic Principles in Nucleic Acid Chemistry—Chemical Reactions of Polynucleotides and Nucleic Acids,*" Academic Press, (1974) vol. II, 1-90 (ISBN 0-12-701902-2(v. 2)).
Sellner, et al., 1998, "Comparison of Three RT-PCR Methods." *Biotechniques*, 25(2): 230-234.
Abramson, Richard D.; "Thermostable DNA Polymerases"; 1999, *PCR Strategies*, pp. 39-57.
Abramson, Richard D.; "Thermostable DNA Polymerases: An Update"; 1999, *PCR Applications: Protocols for Functional Genomics*, pp. 33-48.
Landre, P.A. et al.; "The Use of Cosolvents to Enhance Amplification by the Polymerase Chain Reaction"; 1989, *PCR Strategies*, pp. 3-16.
Lawyer, Frances C. et al.; "Isolation, Characterization, and Expression in *Escherichia coli* of the DNA Polymerase Gene from *Thermus aquaticus*"; 1989, *The Journal of Biological Chemistry*, vol. 264, No. 11, pp. 6427-6437.
Reeve, et al., "A Novel Thermostable Polymerase for DNA Sequencing," *Nature*, 1995, vol. 376, pp. 796-797.

* cited by examiner

*Primary Examiner*—Jeanine A. Goldberg
(74) *Attorney, Agent, or Firm*—Townsend & Townsend & Crew, LLP; Christopher C. Sappenfiel; Charles M. Doyle

(57) ABSTRACT

The present invention relates to improved reverse transcription methods using a modified thermostable DNA polymerases, particularly in a magnesium ion buffer. These methods are particularly useful in combined reverse-transcription/amplification reactions.

29 Claims, No Drawings

SEQUENCE LISTING

<160> NUMBER OF SEQ ID NOS: 21

<210> SEQ ID NO 1
<211> LENGTH: 11
<212> TYPE: PRT
<213> ORGANISM: Artificial Sequence
<220> FEATURE:
<223> OTHER INFORMATION: sequence motif
<221> NAME/KEY: VARIANT
<222> LOCATION: (2)..(2)
<223> OTHER INFORMATION: X is S or A
<221> NAME/KEY: VARIANT
<222> LOCATION: (3)..(3)
<223> OTHER INFORMATION: X is any amino acid
<221> NAME/KEY: VARIANT

```
<222> LOCATION: (4)..(4)
<223> OTHER INFORMATION: X is any amino acid
<221> NAME/KEY: VARIANT
<222> LOCATION: (5)..(5)
<223> OTHER INFORMATION: X is L or I
<221> NAME/KEY: VARIANT
<222> LOCATION: (6)..(6)
<223> OTHER INFORMATION: X is any amino acid
<221> NAME/KEY: VARIANT
<222> LOCATION: (7)..(7)
<223> OTHER INFORMATION: X is any amino acid
<221> NAME/KEY: VARIANT
<222> LOCATION: (8)..(8)
<223> OTHER INFORMATION: X is any amino acid
<221> NAME/KEY: VARIANT
<222> LOCATION: (9)..(9)
<223> OTHER INFORMATION: X is any amino acid
<221> NAME/KEY: VARIANT
<222> LOCATION: (10)..(10)
<223> OTHER INFORMATION: X is any amino acid

<400> SEQUENCE: 1

Leu Xaa Xaa Xaa Xaa Xaa Xaa Xaa Xaa Xaa Glu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: sequence motif
<221> NAME/KEY: VARIANT
<222> LOCATION: (3)..(3)
<223> OTHER INFORMATION: X is Q or G
<221> NAME/KEY: VARIANT
<222> LOCATION: (6)..(6)
<223> OTHER INFORMATION: X is S or A

<400> SEQUENCE: 2

Leu Ser Xaa Glu Leu Xaa Ile Pro Tyr Glu Glu
1               5                   10

<210> SEQ ID NO 3
<211> LENGTH: 11
<212> TYPE: PRT
<213> ORGANISM: Artificial Sequence
<220> FEATURE:
<223> OTHER INFORMATION: sequence motif

<400> SEQUENCE: 3

Leu Ser Gln Glu Leu Ala Ile Pro Tyr Glu Glu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: sequence motif
<221> NAME/KEY: VARIANT
<222> LOCATION: (3)..(3)
<223> OTHER INFORMATION: X is Q or G

<400> SEQUENCE: 4

Leu Ser Xaa Glu Leu Ser Ile Pro Tyr Glu Glu
1               5                   10

<210> SEQ ID NO 5
<211> LENGTH: 11
<212> TYPE: PRT
<213> ORGANISM: Artificial Sequence
```

```
<220> FEATURE:
<223> OTHER INFORMATION: sequence motif
<221> NAME/KEY: VARIANT
<222> LOCATION: (7)..(7)
<223> OTHER INFORMATION: X is V or I

<400> SEQUENCE: 5

Leu Ser Val Arg Leu Gly Xaa Pro Val Lys Glu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: sequence motif

<400> SEQUENCE: 6

Leu Ser Lys Arg Ile Gly Leu Ser Val Ser Glu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: sequence motif
<221> NAME/KEY: VARIANT
<222> LOCATION: (8)..(8)
<223> OTHER INFORMATION: X is S or T

<400> SEQUENCE: 7

Leu Ala Gln Asn Leu Asn Ile Xaa Arg Lys Glu
1               5                   10

<210> SEQ ID NO 8
<211> LENGTH: 11
<212> TYPE: PRT
<213> ORGANISM: Thermus aquaticus

<400> SEQUENCE: 8

Leu Ser Gln Glu Leu Ala Ile Pro Tyr Glu Glu
1               5                   10

<210> SEQ ID NO 9
<211> LENGTH: 11
<212> TYPE: PRT
<213> ORGANISM: Thermus flavus

<400> SEQUENCE: 9

Leu Ser Gly Glu Leu Ser Ile Pro Tyr Glu Glu
1               5                   10

<210> SEQ ID NO 10
<211> LENGTH: 11
<212> TYPE: PRT
<213> ORGANISM: Thermus thermophilus

<400> SEQUENCE: 10

Leu Ser Gln Glu Leu Ala Ile Pro Tyr Glu Glu
1               5                   10

<210> SEQ ID NO 11
<211> LENGTH: 11
<212> TYPE: PRT
<213> ORGANISM: Thermus sp. Z05
```

```
<400> SEQUENCE: 11

Leu Ser Gln Glu Leu Ala Ile Pro Tyr Glu Glu
1               5                   10

<210> SEQ ID NO 12
<211> LENGTH: 11
<212> TYPE: PRT
<213> ORGANISM: Thermus sp. sps17

<400> SEQUENCE: 12

Leu Ser Gln Glu Leu Ser Ile Pro Tyr Glu Glu
1               5                   10

<210> SEQ ID NO 13
<211> LENGTH: 11
<212> TYPE: PRT
<213> ORGANISM: Thermus caldophilus

<400> SEQUENCE: 13

Leu Ser Gln Glu Leu Ala Ile Pro Tyr Glu Glu
1               5                   10

<210> SEQ ID NO 14
<211> LENGTH: 11
<212> TYPE: PRT
<213> ORGANISM: Thermus filiformis

<400> SEQUENCE: 14

Leu Ser Gln Glu Leu Ser Ile Pro Tyr Glu Glu
1               5                   10

<210> SEQ ID NO 15
<211> LENGTH: 11
<212> TYPE: PRT
<213> ORGANISM: Thermotoga maritima

<400> SEQUENCE: 15

Leu Ser Val Arg Leu Gly Val Pro Val Lys Glu
1               5                   10

<210> SEQ ID NO 16
<211> LENGTH: 11
<212> TYPE: PRT
<213> ORGANISM: Thermotoga neapolitana

<400> SEQUENCE: 16

Leu Ser Val Arg Leu Gly Ile Pro Val Lys Glu
1               5                   10

<210> SEQ ID NO 17
<211> LENGTH: 11
<212> TYPE: PRT
<213> ORGANISM: Thermosipho africanus

<400> SEQUENCE: 17

Leu Ser Lys Arg Ile Gly Leu Ser Val Ser Glu
1               5                   10

<210> SEQ ID NO 18
<211> LENGTH: 11
<212> TYPE: PRT
<213> ORGANISM: Bacillus caldotenax

<400> SEQUENCE: 18
```

```
-continued

Leu Ala Gln Asn Leu Asn Ile Ser Arg Lys Glu
1               5                   10

<210> SEQ ID NO 19
<211> LENGTH: 11
<212> TYPE: PRT
<213> ORGANISM: Bacillus stearothermophilus

<400> SEQUENCE: 19

Leu Ala Gln Asn Leu Asn Ile Thr Arg Lys Glu
1               5                   10

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cgagatccct ccaaaatcaa                                              20

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
catgagtcct tccacgatac caa                                          23
```

HIGH TEMPERATURE REVERSE TRANSCRIPTION USING MUTANT DNA POLYMERASES

This application claims the benefit under 35 U.S.C. §119 (e) of U.S. Provisional Application No. 60/198,336, filed Apr. 18, 2000.

BACKGROUND OF THE INVENTION

1. Field of the Invention

The present invention relates to the field of molecular biology and, in particular, relates to methods for the reverse transcription and amplification of ribonucleic acid (RNA) sequences.

2. Description of Related Art

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

The term "DNA polymerase" describes a class of polymerases characterized as DNA-dependent DNA polymerases. DNA polymerase show a strong discrimination against using an RNA template, as expected from their functions in vivo. Nevertheless, several laboratories have shown that some DNA polymerases are capable of in vitro reverse transcription of RNA (Karkas, 1973, Proc. Nat. Acad. Sci. USA 70:3834–3838; Gulati et al., 1974, Proc. Nat. Acad. Sci. USA 71:1035–1039; and Wittig and Wittig, 1978, Nuc. Acid Res. 5:1165–1178). Gulati et al. found that E. coli Pol I could be used to transcribe Qβ viral RNA using oligo(dT) 10 as a primer. Wittig and Wittig have shown that E. coli Pol I can be used to reverse transcribe tRNA that has been enzymatically elongated with oligo(dA). However, as Gulati et al. demonstrated, the amount of enzyme required and the small size of the cDNA product suggests that the reverse transcriptase activity of E. coli Pol I has little practical value.

T. aquaticus (Taq) DNA polymerase, a thermostable DNA polymerase, has been reported to inefficiently synthesize cDNA using $Mg^{+2}$ as the divalent metal ion (Jones and Foulkes, 1989, Nuc. Acids. Res. 176:8387–8388). Tse and Forget, 1990, Gene 88:293–296; and Shaffer et al., 1990, Anal. Biochem. 190:292–296, have described methods for amplifying RNA using Taq DNA polymerase and $Mg^{+2}$ ion. However, the methods are inefficient and insensitive.

Amplification of nucleic acid sequences, both RNA and DNA, is described in U.S. Pat. Nos. 4,683,195; 4,683,202; and 4,965,188; each incorporated herein by reference. A preferred method, the polymerase chain reaction (PCR), typically is carried out using a thermostable DNA polymerase, such as Taq DNA polymerase, which is able to withstand the temperatures used to denature the amplified product in each cycle. PCR is now well known in the art and has been described extensively in the scientific literature. See, for example, PCR Applications, 1999, (Innis et al., eds., Academic Press, San Diego), PCR Strategies, 1995, (Innis et al., eds., Academic Press, San Diego); PCR Protocols, 1990, (Innis et al., eds., Academic Press, San Diego); and PCR Technology, 1989, (Erlich, ed., Stockton Press, New York); each incorporated herein by reference. Commercial vendors, such as PE Biosystems (Foster City, Calif.) market PCR reagents and publish PCR protocols. A review of amplification methods is provided in Abramson and Myers, 1993, Current Opinion in Biotechnology 4:41–47, incorporated herein by reference.

Because reverse transcription using Taq DNA polymerase in a magnesium ion buffer was too inefficient to be practical, PCR amplification starting with an RNA template initially was carried out by first reverse-transcribing the target RNA using, for example, a non-thermostable viral reverse transcriptase such as Molony Murine Leukemia Virus Reverse Transcriptase (MoMuLV RT) or AMV-RT, and then amplifying the resulting cDNA using a thermostable DNA polymerase.

A significant advance was achieved with the discovery that a thermostable DNA polymerase could be used to efficiently reverse transcribe an RNA template by carrying out the reaction in a manganese buffer ($Mn^{+2}$), rather than a magnesium ($Mg^{+2}$) buffer, as is preferred for primer extension using a DNA template. Efficient $Mn^{+2}$-activated reverse transcription using a thermostable DNA polymerase is described in U.S. Pat. Nos. 5,310,652; 5,322,770; 5,407,800; 5,641,864; 5,561,058; and 5,693,517, all incorporated herein by reference. As both the synthesis of cDNA from an RNA template and the synthesis of DNA from a DNA template can be carried out in a $Mn^{+2}$ buffer, the use of a $Mn^{+2}$ buffer enables single-enzyme, coupled reverse transcription/amplification reactions (see also Myers and Sigua, 1995, in PCR Strategies, supra, chapter 5).

SUMMARY OF INVENTION

The present invention provides methods of reverse transcribing RNA sequences using a thermostable DNA polymerase. The present invention further provides methods for reverse transcribing and amplifying RNA sequences, preferably using a single thermostable DNA polymerase in a coupled, one-tube reaction. The methods of the present invention provide improved reverse transcription ("RT") efficiency relative to previously described high-temperature reverse transcription methods.

In a preferred embodiment, the invention provides methods of reverse transcribing RNA sequences in a magnesium ion ($Mg^{+2}$) buffer and, further, methods for reverse transcribing and amplifying RNA sequences using a single thermostable DNA polymerase in a $Mg^{+2}$ buffer, preferably in a coupled, one-tube reaction. The methods carried out using a $Mg^{+2}$ buffer provide enhanced fidelity over previously described methods that rely on manganese ($Mn^{+2}$) activation of a thermostable DNA polymerase.

The methods of the present invention use a mutant thermoactive, preferably thermostable, DNA polymerase that contains a point mutation in a critical amino acid position previously described as affecting the DNA polymerase's ability to incorporate dideoxynucleotides (dd-NTP's) labeled with fluorescein or cyanine family dyes. The present invention results from the surprising discovery that these mutant DNA polymerases also exhibit a significantly increased ability to carry out reverse transcription, particularly in a $Mg^{+2}$ buffer.

Mutant DNA polymerases useful in the methods of the present invention are described in European Patent Publication No. 0 902,035, co-pending U.S. application Ser. No. 09/146,631, and PCT International Patent Publication No. WO 98/40496, each incorporated herein by reference. These mutant DNA polymerases are described as exhibiting an increased ability to incorporate nucleotides, including deoxynucleotides (dNTP's) and base analogues such as dideoxynucleotides (ddNTP's), labeled with fluorescein and cyanine family dyes. For convenience, these mutant DNA polymerases are referred to herein as "fluorescein family dye incorporating" DNA polymerases, or "FDI" DNA polymerases. The primary utility described for FDI DNA polymerases is in DNA sequencing reactions that use dye-terminators (dye labeled ddNTP's) labeled with fluorescein or cyanine family dyes. Because a wild-type DNA polymerase discriminates against nucleotide analogues, and even more so against labeled nucleotide analogues, dye-terminator sequencing reactions typically were carried out using an excess of dye-terminators. By decreasing the discrimination against the labeled dye-terminators, FDI DNA polymerases permit sequencing reactions to be carried out with a significantly lower concentration of dye-terminators.

The critical amino acid position that is mutated in the DNA polymerases used in the present methods, which is the same critical amino acid that affects the DNA polymerase's ability to incorporate dideoxynucleotides labeled with fluorescein and cyanine family dyes, is identified in European Patent Publication No. 0 902,035, and co-pending U.S. application Ser. No. 09/146,631 by its location within a conserved sequence motif present in the native form of the enzyme. Examples of the sequence motif in a number of DNA polymerases is provided therein in Table 1. The sequence motif and the critical amino acid are identified below in essentially the same manner.

Described most generally, using the standard single-letter abbreviations for amino acids, this critical motif in the native form of the DNA polymerase comprises the amino acid sequence

LXXXXXXXXXE        (SEQ ID NO:1), wherein X at position 2 is S or A, X at positions 3, 4, 6, 7, 8, 9, and 10 are any amino acid, and X at position 5 is L or I.

In a more specific embodiment, the critical motif in the native form of the DNA polymerase comprises the amino acid sequence

LSXELXIPYEE        (SEQ ID NO:2), wherein X at position 3 is Q or G, and X at position 6 is S or A. Examples of DNA polymerases containing this motif are DNA polymerases from the genus *Thermus*.

In a preferred embodiment, the critical motif in the native form of the DNA polymerase comprises the amino acid sequence

LSQELAIPYEE        (SEQ ID NO:3).

Examples of DNA polymerases containing this motif are DNA polymerases from *Thermus* species *aquaticus, thermophilus, ZO5,* and *caldophilus*.

In another preferred embodiment, the critical motif in the native form of the DNA polymerase comprises the amino acid sequence

LSXELSIPYEE        (SEQ ID NO:4), wherein X at position 3 is Q or G. Examples of DNA polymerases containing this motif are DNA polymerases from *Thermus* species *flavus*, sps17, and *filiformis*.

In another more specific embodiment, the critical motif in the native form of the DNA polymerase comprises the amino acid sequence

LSVRLGXPVKE        (SEQ ID NO:5);

wherein X at position 7 is V or I. Examples of DNA polymerases containing this motif are DNA polymerases from Thermotoga species *maritima* and *neopolitana*.

In another more specific embodiment, the critical motif in the native form of the DNA polymerase comprises the amino acid sequence

LSKRIGLSVSE        (SEQ ID NO:6).

An example of a DNA polymerase containing this motif is the DNA polymerases from *Thermosipho africanus*.

In another more specific embodiment, the critical motif in the native form of the DNA polymerase comprises the amino acid sequence

LAQNLNIXRKE        (SEQ ID NO:7), wherein X at position 8 is S or T. Examples of DNA polymerases containing this motif are DNA polymerases from *Bacillus* species *caldotenax* and *stearothermophilus*.

In each of the critical motifs identified above, the critical amino acid is at amino acid position 4.

As demonstrated in the examples, mutation of the critical amino acid to any amino acid other than E (present in the native DNA polymerase used in the examples), A, G. or P provided improved RT efficiency. Thus, the methods of the present invention use a thermoactive, preferably thermostable, mutant DNA polymerase characterized in that the native form of the DNA polymerase comprises a sequence motif selected from the group consisting of SEQ ID NOS: 1–7, and the amino acid at position 4 of the motif is mutated to any amino acid other than E, A, G, or P. Preferably, the critical amino acid is mutated to any amino acid other than E, A, G, P, or Q, more preferably to any amino acid other than E, A, G, P, Q, or D.

One aspect of the invention relates to methods of reverse transcribing an RNA, which comprises carrying out a reverse transcription reaction using a mutant thermoactive or thermostable DNA polymerase as described herein. Preferably, the methods comprise:

(a) providing a reaction mixture comprising a primer sufficiently complementary to the RNA to hybridize therewith and initiate synthesis of a cDNA molecule complementary to the target RNA and a mutant thermoactive or thermostable DNA polymerase as described herein; and (b) treating the reaction mixture under appropriate conditions to provide single-stranded cDNA.

In a preferred embodiment, the reaction of step (a) is carried out in an appropriate buffer, wherein the buffer comprises $Mg^{+2}$.

Another aspect of the invention relates to methods for amplifying an RNA, which comprise carrying out a single-enzyme, combined reverse transcription/amplification reaction using a mutant thermoactive or thermostable DNA polymerase as described herein. Preferably, the methods comprise:

(a) providing a reaction mixture comprising a first and second primer, wherein the first primer is sufficiently complementary to the target RNA to hybridize therewith and initiate synthesis of a cDNA molecule complementary to the target RNA, and the second primer is sufficiently homologous to the target RNA to hybridize to the cDNA and initiate synthesis of an extension product, and a mutant thermoactive or thermostable DNA polymerase as described herein, in an appropriate buffer, wherein the buffer comprises $Mg^{+2}$;

(b) treating the reaction mixture under appropriate conditions to provide single-stranded cDNA; and (c) treating the reaction mixture of step (b) under appropriate conditions to amplify the cDNA of step (b).

In a preferred embodiment, the reverse transcription and amplification is carried out as a single-enzyme, one-tube, coupled reverse transcription/PCR amplification reaction using a mutant thermoactive or thermostable DNA polymerase as described herein in a buffer comprising $Mg^{+2}$.

DETAILED DESCRIPTION OF THE INVENTION

To aid in understanding the invention, several terms are defined below.

The term "thermoactive DNA polymerase", as used herein, refers to a DNA polymerase that has an elevated temperature reaction optimum. The thermoactive enzyme used in the present invention catalyzes primer extension optimally at a temperature between 60 and 90° C.

The term "thermostable DNA polymerase" refers to a DNA polymerase that is stable to heat, i.e., does not become irreversibly denatured (inactivated) when subjected to the elevated temperatures for the time necessary to effect denaturation of double-stranded nucleic acids. The heating conditions necessary for nucleic acid denaturation are well known in the art. As used herein, a thermostable polymerase is suitable for use in a temperature cycling reaction such as the polymerase chain reaction ("PCR") amplification methods described in U.S. Pat. No. 4,965,188, incorporated herein by reference.

A "high-temperature reverse transcription reaction", as used herein, refers to a reverse transcription reaction carried out at a temperature at least 40° C., preferably, 40° C.–80° C., and more preferably 50° C.–70° C.

The term "gene" refers to a DNA sequence that comprises control and coding sequences necessary for the production of a recoverable bioactive polypeptide or precursor.

The term "native" refers to a gene or gene product which is isolated from a naturally occurring source. This term also refers to a recombinant form of the native protein produced by molecular biological techniques which has an amino acid sequence identical to that of the native form.

The term "mutant" refers to a gene that has been altered in its nucleic acid sequence or a gene product which has been altered in its amino acid sequence, resulting in a gene product which may have altered functional properties when compared to the native or wild-type gene or gene product. Such alterations include point mutations, deletions and insertions.

As used herein, a "point mutation" in an amino acid sequence refers to either a single amino acid substitution or single amino acid deletion. A point mutation preferably is introduced into an amino acid sequence by a suitable codon change in the encoding DNA.

Individual amino acids in a sequence are represented herein as AN, wherein A is the amino acid in the sequence and N is the position in the sequence. Substitution-type point mutations within an amino acid sequence are represented herein as $A_1NA_2$, wherein $A_1$ is the amino acid in the unmutated protein sequence, $A_2$ is the amino acid in the mutated protein sequence, and N is the position in the amino acid sequence. Either the one-letter or three-letter codes are used for designating amino acids (see Lehninger, BioChemistry 2nd ed., 1975, Worth Publishers, Inc. New York, N.Y.: pages 73–75, incorporated herein by reference). For example, a G46D mutation represents a change from glycine to aspartic acid at amino acid position 46. The amino acid positions are numbered based on the full-length sequence of the protein from which the region encompassing the mutation is derived. Representations of nucleotides and point mutations in DNA sequences are analogous.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

Oligonucleotides can be prepared by any suitable method, including, for example, cloning and restriction of appropriate sequences and direct chemical synthesis by a method such as the phosphotriester method of Narang et al., 1979, Meth. Enzymol. 68:90–99; the phosphodiester method of Brown et al., 1979, Meth. Enzymol. 68:109–151; the diethylphosphoramidite method of Beaucage et al., 1981, Tetrahedron Lett. 22:1859–1862; and the solid support method of U.S. Pat. No. 4,458,066, each incorporated herein by reference. Automated synthesis using cyanoethyl phosphoramidite chemistry is preferred. Reagents and instruments are commercially available from, for example, PE Biosystems (Foster City, Calif.) and Pharmacia (Piscataway, N.J.).

The term "primer", as used herein, refers to an oligonucleotide, whether natural or synthetic, which is capable of acting as a point of initiation of synthesis when placed under conditions in which primer extension is initiated. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur.

A "pair of primers", as used herein, refers to a first and second primer selected to function in an amplification reaction, such as a polymerase chain reaction, to amplify a desired target sequence. For example, for use in a coupled reverse transcription/amplification reaction to amplify a target RNA, a pair of primers comprises a first and second primer, wherein the first primer is sufficiently complementary to the target RNA to hybridize therewith and initiate synthesis of a cDNA molecule complementary to the target RNA, and said second primer is sufficiently homologous to said target RNA to hybridize to the cDNA and initiate synthesis of an extension product. The design of primer pairs for the amplification of nucleic acid sequences is well known in the art.

A primer can be labeled, if desired, by incorporating a label detectable by spectroscopic, photochemical, biochemical, immunochemical, or chemical means. For example, useful labels include $^{32}$p, fluorescent dyes, electron-dense reagents, enzymes (as commonly used in ELISA assays), biotin, or haptens and proteins for which antisera or monoclonal antibodies are available.

As used herein the term "cDNA" refers to a copy DNA molecule synthesized using a ribonucleic acid strand (RNA) as a template. The RNA may be mRNA, tRNA, rRNA, or another form of RNA, such as viral RNA. The cDNA may be single-stranded, double-stranded or may be hydrogen-bonded to a complementary RNA molecule as in an RNA/cDNA hybrid.

The term "reverse transcription reaction mixture" refers to an aqueous solution comprising the various reagents used to reverse transcribe a target RNA. These include enzymes, aqueous buffers, salts, oligonucleotide primers, target nucleic acid, and nucleoside triphosphates. Depending upon the context, the mixture can be either a complete or incomplete reverse transcription reaction mixture.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture. In the preferred embodiment of the invention, the amplification reaction is a polymerase chain reaction (PCR) and the amplification reaction mixture is a PCR mixture. As used herein, an amplification reaction mixture encompasses the reaction mixture used for the amplification of an RNA, as in a coupled reverse transcription/amplification reaction.

The term "buffer," as used herein, refers to a solution containing a buffering agent or a mixture of buffering agents and, optionally, a divalent cation and a monovalent cation.

Conventional techniques of molecular biology and nucleic acid chemistry, which are within the skill of the art, are fully explained in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); Basic Methods in Molecular Biology (Elsevier, N.Y.); Current Protocols in Molecular Biology (John Wiley and Sons, N.Y.); and a series, Methods in Enzymology (Academic Press, Inc.), all of which are incorporated herein by reference. All patents, patent applications, and publications mentioned herein, both supra and infra, are incorporated herein by reference.

Mutant DNA Polymerases

The mutant DNA polymerases used in the methods of the present invention contain a point mutation at a critical amino acid position identified in European Patent Publication No. 0 902,035, co-pending U.S. application Ser. No. 09/146,631, and PCT International Patent Publication No. WO 98/40496, each incorporated herein by reference. European Patent Publication No. 0 902,035 and co-pending U.S. application Ser. No. 09/146,631 identify the critical amino acid in terms of its position within a conserved critical sequence motif found in the native DNA polymerase sequence. PCT International Patent Publication No. WO 98/40496 identifies the critical amino acid in Taq DNA polymerase by position number (E681) and in other DNA polymerase by amino acid sequence homology to Taq DNA polymerase. Both methods identify the same critical amino acid position. For clarity of description, the critical amino acid is described herein in terms of its position in the conserved critical sequence motif.

Table 1, reproduced in essence from Table 1 of European Patent Publication No. 0 902,035 and co-pending U.S. application Ser. No. 09/146,631, provides the critical motifs found in a number of representative DNA polymerases (the critical amino acid is highlighted) along with positions of the critical amino acid within the full enzyme sequence. Multiple position numbers are provided where slightly different amino acid sequences for DNA polymerases from the same species have been reported in the literature.

TABLE 1

| Organism | SEQ ID NO: | Critical Motif | Position |
|---|---|---|---|
| Thermus | | | |
| aquaticus | 8 | LSQELAIPYEE | 681 |
| flavus | 9 | LSGELSTPYEE | 679 |
| thermophilus | 10 | LSQELAIPYEE | 683 |
| species Z05 | 11 | LSQELAIPYEE | 683 |
| species sps17 | 12 | LSQELSIPYEE | 679 |
| caldophilus | 13 | LSQELAIPYEE | 683 |
| filformis | 14 | LSQELSIPYEE | 679 |
| Thermotoga | | | |
| maritima | 15 | LSVRLGVPVKE | 744 |
| neapolitana | 16 | LSVRLGIPVKE | 744 |
| Thermosipho | | | |
| africanus | 17 | LSKRTGLSVSE | 743 |
| Bacillus | | | |
| caldotenax | 18 | LAQNLNISRKE | 725, 724 |
| stearothermophilus | 19 | LAQNLNITRKE | 724, 727, 802 |

A number of species possessing a thermoactive DNA polymerase having the critical motif are described in European Patent Publication No. 0 902,035, co-pending U.S. application Ser. No. 09/146,631, and PCT International Patent Publication No. WO 98/40496. Preferred DNA polymerases for use in the present invention are derived from a Thermus species.

The mutant DNA polymerase used in the methods of the present invention is a thermoactive, preferably thermostable, mutant DNA polymerase characterized in that the native form of the DNA polymerase comprises a sequence motif selected from the group consisting of SEQ ID NOS:1–7, and the amino acid at position 4 of the motif is mutated to any amino acid other than E, A, G, or P. Preferably, the critical amino acid is mutated to any amino acid other than E, A, G, P, or Q, more preferably to any amino acid other than E, A, G, P, Q, or D.

The mutant DNA polymerase can be derived from any species possessing a thermoactive DNA polymerase having the critical motif in the polymerase domain. The critical motif identifies a particular functional region within the polymerase domain of the enzyme, and identifies an amino acid within the motif that is critical to the function. The examples describe the effects on $Mg^{+2}$-activated reverse transcription efficiency of each possible mutation at this site in one widely used thermostable DNA polymerase, Thermus thermophilus DNA polymerase. Just as amino acid changes at this site affect the efficiency of incorporation of dideoxynucleotides (ddNTP's) labeled with fluorescein or cyanine family dyes in essentially all DNA polymerases having the conserved critical motif, it is expected that amino acid changes at this site will affect the $Mg^{+2}$-activated reverse transcription efficiency of essentially all DNA polymerases having the conserved critical motif.

Also within the scope of this invention is the method of the invention performed using thermostable DNA polymerase enzymes having a critical motif which is not derived by mutation, but which critical motif exists as a natural variant.

The structural relatedness of DNA polymerases and the presence of conserved functional domains is well known (see, for example, Ito and Braithwaite, 1991, Nucl. Acids Res. 19(15):4045-4-47; Blanco et al. 1991, Gene 100:27–38; Gutman and Minton, 1993, Nucl. Acids. Res. 21(18):4406–4407; and Delarue et al., 1990, Protein Engineering 3(6):461–467; each incorporated herein by reference). Mutations of a critical amino acid within a conserved functional domain, in general, are expected to have analogous effects when introduced into other DNA polymerases (see, for example, Xu et al., 1997, J. Mol. Biol. 268: 284–302; U.S. Pat. Nos. 5,466,591; 5,795,762; 5,939,292; and 5,614,365; each incorporated herein by reference).

Additional thermoactive or thermostable DNA polymerases containing the critical motif, and the position of the critical amino acid therein, can be identified routinely by direct inspection of the amino acid sequence. Additionally, the critical motif and amino acid can be identified by sequence homology with another DNA polymerase known to contain the critical motif, such as the DNA polymerases from the *Thermus* species listed in Table 1. Amino acid and nucleic acid sequence alignment programs are readily available. For example, widely used sequence alignment programs, including "GAP," "BESTFIT," and "PILEUP," are available from the Genetics Computer Group (Madison, Wis.). In general, carrying out a sequence alignment using the default parameters facilitates identification of the critical amino acid in a DNA polymerase sequence homologous to the critical amino in one of the DNA polymerases listed in Table 1.

As new DNA polymerase sequences are obtained, sequences may be discovered that contain a variant of the critical motif that is not literally described by SEQ ID NO:1, but is identifiable by sequence homology with the known enzymes. As a hypothetical example, an enzyme having a motif in the DNA polymerase domain that is a variant of SEQ ID NO:3, differing only in that the amino acid at position 5 is other than L or I, would be recognized as having the critical motif in view of the high homology (10 out of 11 amino acids in this example) with the critical motif of several *Thermus* species enzymes. Such an enzyme is considered equivalent for the purposes of the present invention.

The critical amino acid is identified with reference to the native enzyme. However, this is not meant to restrict the amino acid sequence of the mutant enzyme everywhere else to that of the native enzyme. Mutant DNA polymerases used in the methods of the present invention may contain additional mutations whose presence may be advantageous for particular applications. For example, mutations which eliminate 5' to 3' exonuclease activity or 3' to 5' exonuclease activity and their applications are well known. An additional substitution mutation in position 3 of the critical motifs identified as SEQ ID NOS:1–7 (for example, a Q682K, E683K mutant of Tth DNA polymerase) may provide additional benefits, particularly in $Mn^{+2}$-activated reactions, such as allowing a further reduction of the $Mn^{+2}$ concentration or further broadening the range of usable salt concentrations.

Mutant DNA polymerases for use in the methods of present inventions preferably are expressed from recombinant expression vectors in which the coding sequence has been modified to express the particular mutant protein sequence of interest. Methods for introducing point mutations into a coding sequence in an expression plasmid are well known in the art and described in the patent and scientific literature incorporated herein by reference. Detailed protocols are provided in, for example, Sambrook et al., Molecular Cloning: A Laboratory Manual, Cold Spring Harbor, 1989, second edition, chapter 15.51, "Oligonucleotide-mediated mutagenesis," and Ausebel et al., Current Protocols in Molecular Biology (current edition), both of which are incorporated herein by reference. European Patent Publication No. 0 902,035, co-pending U.S. application Ser. No. 09/146,631, and PCT International Patent Publication No. WO 98/40496 teach the construction of appropriate expression vectors and the expression and purification of the resulting mutant DNA polymerase. Following the guidance provided in the cited references, and using only well known techniques, one skilled in the art will be able to prepare any number of expression vectors containing a mutant gene suitable for expressing in any of a variety of host systems mutant DNA polymerases for use in the methods of the present invention.

For use in the present high temperature reverse transcription methods, it is only essential that the DNA polymerase is thermoactive. Because the preparation of cDNA from an RNA template does not involve repeated denaturation cycles at elevated temperatures, it is not essential that enzymes useful in the method are thermostable as well as thermoactive. In the single enzyme, combined reverse transcription/polymerase chain reaction amplification (RT/PCR) methods described in the examples, use of a thermostable DNA polymerase is preferred because the DNA polymerase is subject both to RT conditions and to the PCR conditions, which included repeated denaturation cycles.

Divalent Cation

For reverse transcription, according to the present invention, the reaction is carried out in a mixture containing the RNA template, a primer, and a thermoactive or thermostable mutant DNA polymerase. The reaction mixture typically contains all four deoxyribonucleotide triphosphates (dNTPs) and a buffer containing a divalent cation and a monovalent cation. DNA polymerases require a divalent cation for catalytic activity. For extension reactions using a DNA template, the preferred divalent cation is $Mg^{+2}$, although other cations, such as $Mn^{+2}$ or $Co^{+2}$ can activate DNA polymerases.

In contrast to extension reactions using a thermoactive or thermostable DNA polymerase and a DNA template, extension reactions using an RNA template, i.e., reverse-transcription, essentially have required the use of $Mn^{+2}$ in order to achieve useful efficiency. For example, the use of $MnCl_2$ or $Mn(OAc)_2$ for RNA amplification with Tth DNA polymerase provides an increase in sensitivity of at least $10^6$-fold compared to the use of $MgCl_2$ and standard PCR conditions.

The use of $Mn^{+2}$, although it increases the efficiency of reverse transcription, also decreases the fidelity, resulting in an increased number of misincorporated nucleotides. The use of $Mn^{+2}$ also decreases the fidelity of DNA amplifications. Thus, single-enzyme, one-tube RNA amplification reactions using $Mn^{+2}$ suffer reduced fidelity in both the RNA and DNA phases of the reaction. Thus, when higher fidelity RNA amplification is desired, it is preferable to carry out the reaction in two stages. This is achieved by effectively removing the $Mn^{+2}$ ions from the reverse-transcription mixture using a chelator, such as EDTA or, preferably, EGTA, and then adding an appropriate $Mg^{+2}$-containing DNA amplification mixture to complete the reaction.

The use of the mutant DNA polymerases in the methods of the present invention provide benefits for reverse transcription reactions regardless of the divalent cation used. In $Mn^{+2}$ reactions, the use of the mutant DNA polymerase provides for high temperature reverse-transcription and amplification of RNA with a higher efficiency than achieved using the native enzyme. In addition, the use of the mutant DNA polymerase allows carrying out the reaction at a lower $Mn^{+2}$ concentration, thereby minimizing the deleterious effect of $Mn^{+2}$ concentration on fidelity.

Particularly surprising is that the mutant DNA polymerases enable reverse transcription to be carried out using $Mg^{+2}$ with significantly increased efficiency. The use of $Mg+^2$, the enzyme's preferred divalent cation, provides for significantly higher fidelity. Thus, in $Mg^{+2}$ reactions, the use of the mutant DNA polymerase provides for high temperature, high fidelity reverse-transcription and amplification of RNA with a usable efficiency.

The divalent cation is supplied in the form of a salt such $MgCl_2$, $Mg(OAc)_2$, $MgSO_4$, $MnCl_2$, $Mn(OAc)_2$, or $MnSO_4$. In general, for reactions using $Mn^{+2}$, usable cation concentrations in a Tris-HCl buffer will be in a range from 0.5 to 7 mM $MnCl_2$, preferably between 0.5 and 2 mM, and in a bicine/KOAc buffer or tricine/KOAc buffer will be in a range from 0.5 to 20 mM $Mn(OAc)_2$, preferably between 0.5 and 5 mM. In general, for reactions using $Mg^{+2}$, usable divalent cation concentrations in a Tris-HCl buffer will be in a range from 0.5 to 10 mM $MgCl_2$, and in a bicine/KOAc or tricine/KOAC buffers, will be in a range from 0.5 to 20 mM for $Mg(OAc)_2$, preferably between 0.5 and 5 mM. These concentrations provide useful starting conditions for carrying out routine reaction optimization. The optimal divalent ion concentration in a particular reaction will depend not only on the particular enzyme used, but also on the other reaction components, such as, for example, the dNTP concentration and primer sequence and concentration. One of skill will understand that reaction conditions in general, and the divalent cation concentration in particular, can be optimized empirically for any particular reaction using routine experimental methods.

Previously, while capable of activating RNA template-directed DNA synthesis, mixed divalent cation buffers (e.g., $Mn^{+2}$ and $Mg^{+2}$), were not preferred due to reduced sensitivity and efficiency. It is expected that mixed divalent cation buffers are useful in the methods of the present invention and, in some applications, may be preferable. Mixed cation use may enable, for example, a tradeoff between a higher efficiency, but lower fidelity $Mn^{+2}$-activated reaction and a higher fidelity $Mg^{+2}$-activated reaction.

Reverse Transcription and Amplification Methods

High temperature reverse transcription methods and combined reverse transcription/amplification methods using a thermostable DNA polymerase in a $Mn^{+2}$ buffer are well known in the art. See, for example, U.S. Pat. Nos. 5,310,652; 5,322,770; 5,407,800; 5,561,058; 5,641,864; and 5,693,517; each incorporated herein by reference. The methods of the present invention represent a modification of the previously described methods, wherein the modification involves the use of mutant DNA polymerases, as described above. In a preferred embodiment, the reaction is carried out in buffer containing $Mg^{+2}$ as the divalent cation used to activate the DNA polymerase.

One advantage of the present methods is that the use of the mutant DNA polymerases appears to provide faster RT extension rates and, consequently, less time is needed for the RT reaction. Preferably, to maximize the amount of cDNA produced in a reverse transcription reaction, the reaction is carried out for about 30 minutes. Depending on the application, particularly in manganese reactions, RT times as short as one minute or less may provide acceptable results.

Other advantages of the present methods are that the use of the mutant DNA polymerases may provide improved RT efficiency at lower enzyme concentrations and, furthermore, provide a wider range of usable salt concentrations. It is expected that optimal reaction conditions will depend on, for example, the particular enzyme used and can be determined empirically in a routine manner.

Other aspects required to carry out the present methods, such as selection of a target RNA, sample preparation, primer design, and choice of reagents and reaction conditions other than the DNA polymerase and divalent cation used to activate the DNA polymerase are well known in the art and described in, for example, the above-referenced patents. Similarly, if the reverse transcription is coupled with an amplification reaction, all aspects of the amplification not relating to the DNA polymerase and divalent cation used to activate the DNA polymerase are well known in the art and described in, for example, the above-referenced patents. Finally, applications of reverse transcription and amplification of RNA are well known in the art and described in, for example, the above-referenced patents. One of skill in the art will be able to apply the present methods in any application in which the reverse transcription and, optionally, amplification of RNA is desired.

The following examples are offered by way of illustration only and should not be construed as intending to limit the invention in any manner.

EXAMPLE 1

Examples of Mutant DNA Polymerase

A series of 19 mutant DNA polymerases were constructed from "native" *Thermus thermophilus* (Tth) DNA polymerase representing all possible mutations in the critical amino acid. As described in European Patent Publication No. 0 902,035 and co-pending U.S. application Ser. No. 09/146,631, Tth DNA polymerase amino acid sequence contains the critical sequence motif represented as SEQ ID NO:3 (which is a particular embodiment of SEQ ID NO:2, which is a narrower embodiment of the general motif, SEQ ID NO:1). The critical amino acid is at position 683 (E683).

The sequence of Tth DNA polymerase and plasmids containing the gene for Tth DNA polymerase are known in the art (see, for example, U.S. Pat. Nos. 5,618,711 and 5,789,224, both incorporated herein by reference). The particular plasmid used in the present example encodes a Tth DNA polymerase also containing a G46E point mutation that eliminates the 5' to 3' exonuclease activity of the enzyme, as described in U.S. Pat. No. 5,466,591, incorporated herein by reference. In addition, the plasmid contains silent nucleotide substitutions that introduce a ClaI recognition and cleavage site encompassing codons 678, 679, and the first nucleotide of 680, without changing the encoded amino acid sequence. The presence of the additional mutation in the 5' to 3' exonuclease domain is believed to have no appreciable effect on the ability of the DNA polymerase to reverse transcribe RNA in a $Mg^{+2}$ buffer; Tth DNA polymerase having the G46E mutation is considered herein as the native DNA polymerase.

Point mutations in the expressed proteins were introduced by mutating the encoding DNA sequence using standard techniques. Essentially, a short fragment of the coding sequence encompassing codon 683 was replaced with a synthetic fragment containing the desired sequence. The short fragment, ~65 nucleotides in length, was excised by digesting the plasmid with restriction enzymes ClaI and HindIII. A synthetic double-stranded DNA insert was synthesized encoding the same amino acid sequence as the excised fragment, but containing the desired mutation in codon 683. The synthetic fragment was then ligated into the digested plasmid, yielding a plasmid containing a mutated codon encoding a full length Tth DNA polymerase having the desired point mutation.

EXAMPLE 2

Reverse Transcription/Amplification Efficiency

The 20 DNA polymerases described in Example 1 (1 native and 19 mutants) were compared for their ability to catalyze reverse transcription/amplification reactions. In overview, coupled, single-enzyme reverse transcription/amplification reactions were carried out with each of the DNA polymerases. The same initial target copy number was used for each reaction, and the synthesis of amplification product was monitored during the reaction. The number of cycles required to generate an arbitrary, but fixed, quantity of amplified product, which provides a measure of the reaction efficiency, was determined for each DNA polymerase. Because the initial reverse transcription step typically is the critical limiting step in a reverse transcription/amplification reaction, an improvement in overall reaction efficiency also suggests an improvement in the initial reverse transcription step.

The increase in amplified nucleic acid during the reaction was monitored using the methods described in Higuchi et al., 1992, Bio/Technology 10:413–417; Higuchi et al., 1993, Bio/Technology 11: 1026–1030; Higuchi and Watson, in PCR Applications, supra, Chapter 16; U.S. Pat. No. 5,994, 056; and European Patent Publication Nos. 487,218 and 512,334, each incorporated herein by reference. These methods, referred to herein as kinetic-PCR, rely on the increased fluorescence that ethidium bromide (EtBr) and other DNA-binding dyes exhibit when bound to double-stranded DNA in order to detect the change in amount of double-stranded DNA in a reaction. The increase of double-stranded DNA resulting from the synthesis of target sequences results in an increase in the amount of dye bound to double-stranded DNA and a concomitant detectable increase in fluorescence.

Amplifications were carried out with ethidium bromide in the reaction. Alternatively, amplifications can be carried out using SYBR® Green I (Molecular Probes, Eugene, Oreg.) in the reaction. Both dyes increase their fluorescence upon intercalation into, or binding to, the double-stranded DNA. The reactions are carried out in a combined thermal cycler and fluorescence detection system which enables monitoring the fluorescence of the reaction mixture during the amplification. It will be clear that, in addition to the instruments described below, any suitable instrument can be used.

RNA Target and Amplification Primers

A target RNA was synthsized using an expression plasmid encoding the human glyceraldehyde-3-phosphate dehydrogenase (GAPDH) gene. A region of the GAPDH RNA was amplified using the following primers, shown in the 5' to 3' orientation:

P1 (SEQ ID NO:20) 5'-CGAGATCCCTCCAAAAT-CAA

P2 (SEQ ID NO:21) 5'-CATGAGTCCTTCCAC-GATACCAA

The initial target concentration was measured by standard means. For the comparison reactions described herein, the absolute copy number is less important than the relative copy number. To insure the same initial copy number in each reaction, aliquots of dilutions of the same initial RNA stock were used.

One of skill will recognize the selection of target is a matter of convenience.

Other RNA targets and corresponding amplification primers could be used in essentially the same protocol. Routine optimization of the reaction conditions would be expected.

Amplification

Each RT-PCR amplification was carried out in a total reaction volume of 100 µl. The final reagent concentrations were as follows:
  10 units DNA polymerase
  $10^6$ copies GAPDH RNA
  50 mM Tricine, pH 8.15
  50 mM KOAc
  2 mM $Mg(OAc)_2$
  200 µM dATP, dGTP, dCTP
  400 µM dUTP
  200 nM each primer
  8% glycerol
  1% DMSO
  1 µg/ml of ethidium bromide
  2 units UNG*

Manufactured by Roche Molecular Systems and commercially available through PE Biosystems, Foster City, Calif.

Alternatively, SYBR® Green I can be used instead of ethidium bromide to enable detection of the amplified product. Amplifications using SYBR® Green I are carried out with 0.2×SYBR® Green I (sold as 10,000×) diluted in DMSO.

Reactions using ethidium bromide preferably are carried out using a ABI PRISM(® 7700 Sequence Detection System (PE Biosystems, Foster City, Calif.), which allows the selection of suitable detection wavelengths. Reactions using SYBR® Green I preferably are carried out using a GeneAmp® 5700 Sequence Detection System (PE Biosystems, Foster City, Calif.) using the same thermal cycling conditions. The GeneAmp® 5700 Sequence Detection System is designed for use with SYBR® Green I and the excitation and detection wavelengths are pre-set for this dye.

The assays described below were carried out using a custom instrument consisting essentially of a GeneAmp® PCR system 9600 thermal cycler (PE Biosystems, Foster City, Calif.) modified by the addition of a fluoresence detection system similar to that used in the GeneAmp® 5700 Sequence Detection System, but designed for use with ethidium bromide. Results obtained using the custom instrument would be expected to be comparable to results obtained using one of the preferred instruments.

Amplification reactions were carried out using the specific temperature cycling profile shown below.

| Thermal Cycling Times and Temperatures | | |
|---|---|---|
| Pre-reaction incubation: | | 50° C. for 2 minutes |
| Reverse-transcription | | 60° C. for 30 minutes |
| | | 95° C. for 1 minute |
| 55 cycles: | denature: | 95° C. for 15 seconds |
| | anneal: | 55° C. for 30 seconds |
| | extend: | 72° C. for 15 seconds |
| Final extension and hold: | | 72° C. |

Detection

The accumulation of amplified product was measured at each cycle during the reaction by measuring the increase in reaction fluorescence. During each amplification cycle, each reaction was excited with light at a wavelength near the excitation maximum of the dye and the emission of the dye was measured near its emission maximum.

Fluorescence measurements were normalized by dividing by an initial fluorescence measurement obtained during a cycle early in the reaction while the fluorescence measurements between cycles appear to be relatively constant. The cycle number chosen for the initial fluorescence measurement was the same for all reactions compared, so that all measurements represent increases relative to the same reaction cycle.

The number of amplification cycles carried out until the fluorescence exceeded an arbitrary fluorescence level (AFL) was calculated from the observed fluorescence values. The AFL was chosen close to the baseline fluorescence level., but above the range of random fluctuations in the measured fluorescence, so that the reaction kinetics were measured during the early phase of the amplification when the amount of product increases geometrically. During this geometric growth phase of the amplification, the number of cycles required to reach a particular threshold value depends solely on the initial copy number and the reaction efficiency. As each reaction is carried out using the same initial target copy number, the number of cycles to reach the threshold provides a measure of the reaction efficiency. In later cycles, accumulation of amplified product and exhaustion of reagents eventually leads to a reaction plateau.

An AFL of 1.12 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ value, was calculated by interpolating fluorescence measurements between cycles.

Result

The $C_T$ values obtained using the native Tth DNA polymerase (E683) and each of the mutant DNA polymerases (identified by amino acid at position 683) are shown in the table, below. Each $C_T$ value represents the average value obtained from two reactions. To facilitate comparison, the difference of the $C_T$ values, ($C_T$ native)–($C_T$ mutant), also is provided. An increase in efficiency using the mutant DNA polymerase results in reaching the threshold value in fewer cycles, i.e., a lower $C_T$ value. Thus, a positive difference in $C_T$ values reflects an increase in efficiency.

| Reaction Efficiencies | | | |
|---|---|---|---|
| aa @ 683 1-letter code | aa @ 683 3-letter code | Ave. $C_T$ | ($C_T$ native)–($C_T$ mutant) |
| E | Glu | 37.7 | 0.0 |
| A | Ala | 38.7 | −1.1 |
| C | Cys | 33.2 | 4.5 |
| D | Asp | 36.6 | 1.1 |
| F | Phe | 28.2 | 9.5 |
| G | Gly | 42.3 | −4.7 |
| H | His | 32.0 | 5.7 |
| I | Ile | 33.4 | 4.3 |
| K | Lys | 27.6 | 10.1 |
| L | Leu | 27.8 | 9.9 |
| M | Met | 30.3 | 7.4 |
| N | Asn | 31.5 | 6.2 |
| P | Pro | 38.8 | −1.1 |
| Q | Gln | 37.4 | 0.3 |
| R | Arg | 27.2 | 10.5 |
| S | Ser | 32.0 | 5.7 |
| T | Thr | 31.5 | 6.2 |
| V | Val | 31.4 | 6.3 |
| W | Trp | 29.2 | 8.5 |
| Y | Tyr | 26.1 | 11.6 |

The results indicate that mutations of the amino acid at position 683 to any amino acid except Ala, Gly, or Pro resulted in an DNA polymerase with increased efficiency. Of these, all but the Asp and Gln mutants resulted in a least a four cycle improvement in the $C_T$ value.

EXAMPLE 3

Reverse Transcription Efficiency

Selected DNA polymerases described in Example 1 were compared for their ability to catalyze reverse transcription reactions. Reverse transcription reactions were carried out with each of the DNA polymerases using either $Mg^{+2}$ or $Mn^{+2}$. The resulting cDNA from each of the reactions then was amplified under identical conditions using the native enzyme and $Mg^{+2}$. This protocol allows measuring the effect of the enzyme specifically on the reverse transcription portion of a reverse transcription/amplification reaction.

In addition to the native enzyme, reactions were carried out using DNA polymerases having mutations to F, K, L, R, and Y at amino acid position 683. Each of these mutations was shown in Example 2 to provide significant increases in efficiency in a combined reverse transcription/amplification reaction.

Reverse Transcription

Each reverse transcription was carried out in a total reaction volume of 100 µl. The final reagent concentrations were as follows:

5 units DNA polymerase $10^6$ copies GAPDH RNA 50 mM Tricine, pH 8.15

50 mM KOAc 2 mM Mg(OAc)$_2$ or Mn(OAc)$_2$

200 µM dATP, dGTP, dCTP, dUTP 200 nM each primer

8% glycerol

1% DMSO 0.2×SYBR® Green I 1 unit UNG*

Manufactured by Roche Molecular Systems and commercially available through PE Biosystems, Foster City, Calif.

The reverse transcription reactions were carried out using the specific temperature cycling profile used is shown below.

| Reverse Transcription Times and Temperatures | |
|---|---|
| Pre-reaction incubation: | 50° C. for 2 minutes |
| Reverse-transcription | 60° C. for 30 minutes |
| Hold: | 4° C. |

Amplification

Following reverse transcription, 10 µl of the reaction products were added to 10 µl 2 mM EGTA to chelate the metal cation, thereby effectively removing it from the following amplification reaction. The mixture was added to a PCR amplification mixture containing the native enzyme and $Mg^{+2}$. Thus, residual mutant DNA polymerase was diluted such that any effects were expected to be negligible. The PCR amplifications were carried out in 100 µl reactions with the following final reagent concentrations:

5 units native DNA polymerase
50 mM Tricine, pH 8.15
50 mM KOAc
2 mM Mg(OAc)$_2$
200 µM dATP, dGTP, dCTP, dUTP
200 nM each primer
8% glycerol
1% DMSO
0.2×SYBR® Green I.

Amplification reactions were carried out using the specific temperature cycling profile shown below.

| Amplification Thermal Cycling Times and Temperatures | | |
|---|---|---|
| 55 cycles: | denature: | 95° C. for 1 minute |
| | anneal: | 95° C. for 15 seconds |
| | extend: | 55° C. for 30 seconds |
| | | 72° C. for 15 seconds |
| Final extension and hold: | | 72° C. |

Results

The $C_T$ values obtained using the native Tth DNA polymerase (E683) and each of the mutant DNA polymerases (identified by amino acid at position 683) for the reverse transcription, and the native Tth DNA polymerase for all amplifications are shown in the table, below. Each $C_T$ value represents the average valve obtained from two reactions. To facilitate comparison, the difference of the $C_T$ values, ($C_T$ native)–($C_T$ mutant), also is provided. An increase in efficiency using the mutant DNA polymerase results in reaching the threshold value in fewer cycles, i.e., a lower $C_T$ value. Thus, a positive difference in $C_T$ values reflects an increase in efficiency.

| aa @ 683 | Ave. $C_T$ | ($C_T$ native)–($C_T$ mutant) |
|---|---|---|
| | Reaction Efficiencies $Mn^{+2}$-activated RT | |
| E | 33.8 | 0.0 |
| F | 26.9 | 6.9 |
| K | 29.0 | 4.8 |
| L | 26.0 | 7.8 |
| R | 25.9 | 7.9 |
| Y | 24.5 | 9.3 |

| aa @ 683 | Ave. $C_T$ | ($C_T$ native)–($C_T$ mutant) |
|---|---|---|
| | Reaction Efficiencies $Mn^{+2}$-activated RT | |
| B | 24.6 | 0.0 |
| F | 21.1 | 3.5 |
| K | 20.2 | 4.4 |
| L | 20.6 | 4.0 |
| R | 20.7 | 3.9 |
| Y | 20.3 | 4.3 |

Each of these mutant DNA polymerase provided a significantly increased efficiency in reverse transcription/amplification reactions. Because the DNA amplification portion of each reaction was carried out identically with the native enzyme, these results demonstrate that each of these mutant DNA polymerase provide increased 10 efficiency in the reverse transcription portion of the reactions. The mutant DNA polymerases provided significantly improved efficiency using either cation.

The improvement was particularly pronounced using $Mg^{+2}$ and demonstrates that the use of the mutant DNA polymerases makes $Mg^{+2}$-activated reactions practical. Consistent with what has been reported previously, RNA amplification using the native enzyme essentially requires the use of $Mn^{+2}$ to achieve a usable reaction efficiency, as seen by the almost 10 cycle delay (33.8–24.6) in the $C_T$ using $Mg^{+2}$. In contrast, using the E683Y mutant, for example, the efficiency of the $Mg^{+2}$-activated reaction was equal to that achieved using the native enzyme and $Mn^{+2}$.

EXAMPLE 4

Fidelity

The fidelities of selected mutant DNA polymerases and the native enzyme were compared in several ways. The fidelities in coupled reverse-transcription/amplification reactions carried out in a $Mg^{+2}$ buffer were compared to the fidelities when carried out in a $Mn^{+2}$ buffer. Additionally, the fidelities of the enzymes when used in DNA amplifications were compared.

The fidelities of DNA polymerases can be compared by measuring the melting temperature (Tm) profile of amplified products generated using the enzymes. The fidelity of a DNA polymerase is reflected in the number of misincorporations occurring during strand synthesis. An amplification using a lower fidelity enzyme will result in greater heterogeneity in the resulting population of amplified sequences. To measure the heterogeneity, the amplified products are denatured, allowed to reanneal, and the Tm of the resulting duplexes is measured. Because the strands in the duplexes are combined at random from a heterogenous population of sequences, the duplexes, in general, contain a number of mismatches. The greater the sequence heterogeneity in the population of amplified products, the greater the average number of mismatches in the duplexes. These mismatches destabilize the duplexes and result in a lower measured Tm.

A melting curve for the amplified products of a kinetic-PCR reaction is carried out conveniently using the thermal cycler/fluorescence detection instrument used in the amplification. After amplification, the relationship between fluorescence and temperature is measured over a temperature range encompassing the denaturation temperature of the product. The transition between double-stranded and single-stranded molecules is reflected in a change in dye fluorescence. Thus, a melting curve can be determined conveniently. Alternatively, measurements can be carried out using standard methods, which typically involve monitoring the change in optical density, a measure of the amount of double-stranded DNA in the reaction, with a change in temperature.

The fidelity of the native DNA polymerase was compared to the fidelities of two of the mutants, DNA polymerases containing the E683K and E683N mutations, respectively. Coupled reverse transcription/amplification reactions were carried out in duplicate in both $Mn^{+2}$ and $Mg^{+2}$ buffers essentially as described in Example 2, but with the following changes. For the $Mn^{+2}$ reactions, 2 mM $Mn(OAc)_2$ was used in the reaction. All reactions were carried out using 25 U of DNA polymerase.

To measure the hybridization stability profile (melting curve) of the amplified double-stranded target sequences, the fluorescence of the post-amplification reaction mixture was monitored over a range of temperatures covering at least 60° C. to 80° C. As expected, the fluorescence measurements resulted in a sigmoidal melting curve. A Tm was defined as the temperature of the inflection point in the sigmoidal melting curve, which corresponds to the temperature at which half the target is in single-stranded form.

Results

The Tm values measured for the amplification products of the $Mg^{+2}$-activated reactions and the $Mn^{+2}$-activated reactions are shown in the table, below. Each measurement reported is the average of replicate reactions. All temperature are degrees Celsius.

| Amplification Product Tm Values | | |
|---|---|---|
| DNA Polymerase | Tm, $Mg^{+2}$ | Tm, $Mn^{+2}$ |
| Native | 80 | 78 |
| E683K | 80 | 76 |
| E683N | 80 | 76 |

Using a $Mg^{+2}$ buffer, no difference in fidelity was observed between the native and the mutant DNA polymerases. Similar reactions carried out using all 20 DNA polymerases (data not shown) confirmed that the fidelity of all the mutant DNA polymerases are identical to the fidelity of the native DNA polymerase in $Mg^{+2}$-activated reactions.

Comparing the results obtained using a $Mg^{+2}$ buffer to those obtained using a $Mg^{+2}$ buffer, the fidelities of the all of the DNA polymerase was reduced, as can be seen from the lower Tm values obtained. Interestingly, the two mutant DNA polymerases exhibited an even lower fidelity than did the native enzyme when using a $Mn^{+2}$ buffer, at least under these reaction conditions.

The fidelity is affected by the $Mn^{+2}$ concentration. To compare the effect of $Mn^{+2}$ concentration on the fidelity of the mutant and native enzymes, additional experiments were carried out using the E683K mutation using a range of $Mn^{+2}$ concentrations from 0.5 to 5 mM. The results (data not shown) showed that, as expected the lowest $Mn^{+2}$ concentration yielded the highest fidelity reactions using either enzyme. The fidelity of the mutant enzyme was more affected by an increased $Mn^{+2}$ concentration than was the fidelity of the native enzyme. Surprisingly, however, at least in these experiments, the mutant enzyme also was most efficient at the lowest $Mn^{+2}$ concentration. Thus, the use of the mutant enzyme allows carrying out the reaction at a lower $Mn^{+2}$ concentration, thereby minimizing the deleterious effect of $Mn^{+2}$ concentration on fidelity.

In addition, both $Mn^{+2}$-activated and $Mg^{+2}$-activated reactions also were carried out essentially as described above, but using DNA templates, which facilitates observing the effect of fidelity in only the DNA portion of the reaction. In all cases, the Tm value of the product of the DNA amplification was indistinguishable from the Tm value of the product of the RNA amplification.

The results, taken together with the results of the previous examples, demonstrate advantages of the methods of the present invention. Previously described high temperature reverse-transcription and amplification methods were carried out using $Mn^{+2}$ to achieve adequate reaction efficiency, but suffered from a reduction in fidelity. The present invention provides several options. Using $Mn^{+2}$, the use of the mutant enzyme provides for high temperature reverse-transcription and amplification of RNA with a higher efficiency than achieved using the native enzyme, and allows carrying out the reaction at a lower $Mn^{+2}$ concentration, thereby minimizing the deleterious effect of $Mn^{+2}$ concentration on fidelity. Using $Mg^{+2}$, the use of the mutant enzyme provides for high temperature, high fidelity reverse-transcription and amplification of RNA with a usable efficiency.

We claim:

1. A method for reverse transcribing an RNA, that comprises:
   (a) providing a reverse transcription reaction mixture comprising said RNA, a primer, Mg+2, and a mutant thermoactive DNA polymerase, wherein said mutant DNA polymerase is characterized in that
      i) in its native form said DNA polymerase comprises a polymerase domain comprising an amino acid sequence that is SEQ ID NO:1, wherein said polymerase domain has the ability to incorporate nucleotides;
      ii) the amino acid at position 2 of said amino acid sequence is S or A and the amino acid at position 5 of said amino acid sequence is L or I; and
      iii) the amino acid at position 4 of said amino acid sequence is mutated in comparison to said native sequence to an amino acid other than E, A, G, or P; and
   (b) treating said reaction mixture at a temperature sufficient for said mutant DNA polymerase to initiate synthesis of an extension product of said primer to provide a cDNA molecule complementary to said RNA.

2. The method of claim 1, wherein said mutant DNA polymerase in its native form comprises an amino acid sequence that is SEQ ID NO:2, the amino acid at position 3 of said amino acid sequence is Q or G, and the amino acid at position 6 of said amino acid sequence is S or A.

3. The method of claim 1, wherein said mutant DNA polymerase in its native form comprises a polymerase domain comprising an amino acid sequence that is SEQ ID NO:3.

4. The method of claim 1, wherein said mutant DNA polymerase in its native form comprises a polymerase domain comprising an amino acid sequence that is SEQ ID NO:4, and the amino acid at position 3 is Q or G.

5. The method of claim 1, wherein said mutant DNA polymerase is thermostable.

6. The method of claim 1, wherein said mutant DNA polymerase is a mutant form of a *Thermus* species DNA polymerase.

7. The method of claim 1, wherein said mutant DNA polymerase is a mutant form of *Thermus thermophilus* DNA polymerase or *Thermus aquaticus* DNA polymerase.

8. The method of claim 1, wherein said temperature of said reaction mixture in step (b) is between 40° C. and 80° C.

9. The method of claim 1, wherein said amino acid at position 4 of said amino acid sequence is mutated in comparison to said native sequence to an amino acid other than E, A, G, P, Q, or D.

10. A method for amplifying an RNA, that comprise:
    (a) reverse transcribing said RNA according to a method of claim 1 to provide a cDNA;
    (b) amplifying said cDNA.

11. The method of claim 10, wherein in step (b) said amplifying is carried out using a polymerase chain reaction.

12. A method for amplifying an RNA using a single-enzyme reverse transcription/amplification reaction, that comprises:
    (a) providing an amplification reaction mixture comprising said RNA, a pair of primers, a divalent cation, and a mutant thermostable DNA polymerase, wherein said mutant DNA polymerase is characterized in that i) in its native form said DNA polymerase comprises a polymerase domain comprising an amino acid sequence that is SEQ ID NO:1, wherein said polymerase domain has the ability to incorporate nucleotides;
ii) the amino acid at position 2 of said amino acid sequence is S or A and the amino acid at position 5 of said amino acid sequence is L or I; and
iii) the amino acid at position 4 of said amino acid sequence is mutated in comparison to said native sequence to an amino acid other than E, A, G, or P; and (b) treating said reaction mixture at a temperature sufficient for said mutant DNA polymerase to initiate synthesis of an extension product of said primer to provide a cDNA molecule complementary to said RNA;

(c) treating said reaction mixture at an appropriate temperature for said mutant DNA polymerase to initiate synthesis of an extension product of said second primer to provide a double-stranded cDNA molecule; and (d) amplifying said double-stranded cDNA molecule of step (c) by a polymerase chain reaction.

13. The method of claim 12, wherein said mutant DNA polymerase in its native form comprises a polymerase domain comprising an amino acid sequence that is SEQ ID) NO:2, the amino acid at position 3 of said amino acid sequence is Q or G, and the amino acid at position 6 of said amino acid sequence is S or A.

14. The method of claim 12, wherein said mutant DNA polymerase in its native form comprises a polymerase domain comprising an amino acid sequence that is SEQ ID NO:3.

15. The method of claim 12, wherein said mutant DNA polymerase in its native form comprises a polymerase domain comprising an amino acid sequence that is SEQ ID NO:4, and the amino acid at position 3 is Q or C.

16. The method of claim 12, wherein said mutant DNA polymerase is thermostable.

17. The method of claim 12, wherein said mutant DNA polymerase is a mutant form of a *Thermus* species DNA polymerase.

18. The method of claim 12, wherein said mutant DNA polymerase is a mutant form of *Thermus thermophilus* DNA polymerase or *Thermus aquaticus* DNA polymerase.

19. The method of claim 12, wherein said temperature of said reaction mixture in step(b) is between 40° C. and 80° C.

20. The method of claim 12, wherein said amino acid at position 4 of said amino acid sequence is mutated in comparison to said native sequence to an amino acid other than E, A, G, P, Q, or D.

21. A method for amplifying an RNA using a single-enzyme reverse transcription/amplification reaction, that comprises:

(a) providing an amplification reaction mixture comprising said RNA, a pair of primers, Mg+2, and a mutant thermostable DNA polymerase, wherein said mutant DNA polymerase is characterized in that
i) in its native from said DNA polymerase comprises a polymerase domain comprising an amino acid sequence that is SEQ ID NO: 1, wherein said polymerase domain has the ability to incorporate nucleotides;
ii) the amino acid at position 2 of said amino acid sequence is S or A and the amino acid at position 5 of said amino acid sequence is L or I; and
iii) the amino acid at position 4 of said amino acid sequence is mutated in comparison to said native sequence to an amino acid other than E, A, G, or P; and (b) treating said reaction mixture at a temperature sufficient for said mutant DNA polymerase to initiate synthesis of an extension product of said primer to provide a cDNA molecule complementary to said RNA;

(c) treating said reaction mixture at an appropriate temperature for said mutant DNA polymerase to initiate synthesis of an extension product of said second primer to provide a double-stranded cDNA molecule; and (d) amplifying said double-stranded cDNA molecule of step (c) by a polymerase chain reaction.

22. The method of claim 21, wherein said mutant DNA polymerase in its native form comprises an amino acid sequence that is SEQ ID) NO:2, the amino acid at position 3 of said amino acid sequence is Q or G, and the amino acid at position 6 of said amino acid sequence is S or A.

23. The method of claim 21, wherein said mutant DNA polymerase in its native form comprises a polymerase domain comprising an amino acid sequence tat is SEQ ID NO:3.

24. The method of claim 21, wherein said mutant DNA polymerase in its native form comprises an amino acid sequence that is SEQ ID NO:4, and the amino acid at position 3 is Q or G.

25. The method of claim 21, wherein said mutant DNA polymerase is thermostable.

26. The method of claim 21, wherein said mutant DNA polymerase is a mutant form of a *Thermus* species DNA polymerase.

27. The method of claim 21, wherein said mutant DNA polymerase is a mutant form of *Thermus thermophilus* DNA polymerase or *Thermus aquaticus* DNA polymerase.

28. The method of claim 21, wherein said temperature of said reaction mixture in step (b) is between 40° C. and 80° C.

29. The method of claim 21, wherein said amino acid at position 4 of said amino acid sequence is mutated in comparison to said native sequence to an amino acid other than E, A, G, P, Q or D.

* * * * *